(12) United States Patent
Li

(10) Patent No.: US 11,661,947 B2
(45) Date of Patent: May 30, 2023

(54) NECK FAN

(71) Applicant: SHENZHEN JISU TECHNOLOGY CO., LTD, Shenzhen (CN)

(72) Inventor: Xiangfu Li, Shenzhen (CN)

(73) Assignee: SHENZHEN JISU TECHNOLOGY CO., LTD, Shenzhen (CN)

( * ) Notice: Subject to any disclaimer, the term of this patent is extended or adjusted under 35 U.S.C. 154(b) by 0 days.

(21) Appl. No.: 17/471,178

(22) Filed: Sep. 10, 2021

(65) Prior Publication Data

US 2022/0106963 A1   Apr. 7, 2022

Related U.S. Application Data

(63) Continuation of application No. PCT/CN2020/128564, filed on Nov. 13, 2020.

(30) Foreign Application Priority Data

Oct. 25, 2019   (CN) .......................... 201921815938.3
Sep. 30, 2020   (CN) .......................... 202022210032.8

(51) Int. Cl.
*F04D 25/16*    (2006.01)
*F04D 29/42*    (2006.01)
(Continued)

(52) U.S. Cl.
CPC ......... *F04D 25/166* (2013.01); *F04D 29/424* (2013.01); *F04D 29/4213* (2013.01);
(Continued)

(58) Field of Classification Search
CPC ............... F04D 29/424; F04D 29/4226; F04D 29/4246; F04D 25/084; F04D 25/08;
(Continued)

(56) References Cited

U.S. PATENT DOCUMENTS 5,802,865 A *   9/1998   Strauss ...................... A61F 7/10
                                                                 62/259.3
6,682,552 B2 *  1/2004   Ramsden .................. A61F 7/10
                                                                 607/114
(Continued)

FOREIGN PATENT DOCUMENTS

CN    201615075 U   10/2010
CN    202001342 U   10/2011
(Continued)

OTHER PUBLICATIONS

Non Final Office Action, U.S. Appl. No. 17/585,594, dated Mar. 30, 2022 (31 pages).

(Continued)

*Primary Examiner* — Courtney D Heinle
*Assistant Examiner* — Andrew J Marien

(57) ABSTRACT

A neck fan includes an arc-shaped housing configured to hang around user's neck and at least four fan assemblies arranged in the housing. The housing includes a first part and a second part. Each of the first part and the second part defines an accommodating space, air inlets and air outlets communicated with the accommodating space, at least one partition is arranged in the accommodating space and configured to divide the accommodating space into at least two accommodating parts arranged along an extension direction of the housing. Each of the fan assemblies is arranged in one of the at least two accommodating parts and is configured to direct air into the one of the at least two accommodating parts through corresponding air inlets and to direct air out of the one of the at least two accommodating parts through corresponding air outlets.

18 Claims, 5 Drawing Sheets

(51) Int. Cl.
*A61F 7/00* (2006.01)
*F04D 29/00* (2006.01)
*F04D 25/06* (2006.01)

(52) U.S. Cl.
CPC .. *F04D 29/4246* (2013.01); *A61F 2007/0011* (2013.01); *A61F 2007/0067* (2013.01); *F04D 25/0673* (2013.01); *F04D 29/005* (2013.01)

(58) Field of Classification Search
CPC ................ F04D 25/166; A41D 20/005; A61F 2007/20009; A61F 2007/001; A61F 2007/0011; A42B 3/286; F24F 2221/38; F24F 7/007
See application file for complete search history.

(56) References Cited

U.S. PATENT DOCUMENTS

| | | | |
|---|---|---|---|
| 10,709,601 | B2 * | 7/2020 | Adair .................. A61F 7/02 |
| 11,187,241 | B1 * | 11/2021 | Liu ..................... F04D 29/441 |
| 11,319,960 | B2 † | 5/2022 | Liu |
| 2011/0240026 | A1 | 10/2011 | Ausen |
| 2011/0259028 | A1 | 10/2011 | Lee |
| 2015/0374046 | A1 | 12/2015 | Peavy et al. |
| 2017/0266038 | A1 * | 9/2017 | Peavy ................ A41D 13/0053 |
| 2017/0370596 | A1 * | 12/2017 | Lee ..................... F04D 25/084 |
| 2019/0234412 | A1 | 8/2019 | Schwimmer et al. |
| 2020/0187574 | A1 * | 6/2020 | Te Hsiang ......... A41D 13/0053 |
| 2020/0240438 | A1 | 7/2020 | Ma et al. |
| 2021/0310718 | A1 | 10/2021 | Zeng et al. |
| 2021/0355959 | A1 † | 11/2021 | Liu |
| 2021/0355963 | A1 | 11/2021 | Kang |
| 2022/0235786 | A1 * | 7/2022 | Liu ..................... F04D 29/4226 |

FOREIGN PATENT DOCUMENTS

| | | | |
|---|---|---|---|
| CN | 205787943 U | 12/2016 | |
| CN | 206386293 U | 8/2017 | |
| CN | 110685939 A | 1/2020 | |
| CN | 210623163 U | 5/2020 | |
| CN | 210829801 U | 6/2020 | |
| CN | 211049811 U | 7/2020 | |
| CN | 211059041 U | 7/2020 | |
| CN | 211116729 U | 7/2020 | |
| CN | 211116731 U | 7/2020 | |
| CN | 211314612 U | 8/2020 | |
| CN | 211692914 U | 10/2020 | |
| CN | 212536129 U | 2/2021 | |
| CN | 212536145 U | 2/2021 | |
| CN | 212563735 U | 2/2021 | |
| CN | 212615494 U | 2/2021 | |
| CN | 212615499 U | 2/2021 | |
| CN | 212615505 U | 2/2021 | |
| CN | 212690406 U | 3/2021 | |
| CN | 212803654 U | 3/2021 | |
| CN | 212867975 U | 4/2021 | |
| CN | 212899050 U | 4/2021 | |
| CN | 213206044 U | 5/2021 | |
| CN | 213206107 U | 5/2021 | |
| CN | 213206109 U | 5/2021 | |
| CN | 213392779 U | 6/2021 | |
| CN | 213392786 U | 6/2021 | |
| CN | 213392811 U | 6/2021 | |
| CN | 213450914 U | 6/2021 | |
| CN | 213450915 U | 6/2021 | |
| CN | 213684600 U | 7/2021 | |
| CN | 213684631 U | 7/2021 | |
| CN | 213928809 U | 8/2021 | |
| CN | 213931250 U | 8/2021 | |
| CN | 213931251 U | 8/2021 | |
| CN | 213931257 U | 8/2021 | |
| CN | 214170903 U | 9/2021 | |
| CN | 214198996 U | 9/2021 | |
| CN | 214404034 U | 10/2021 | |
| CN | 214404047 U | 10/2021 | |
| CN | 214742179 U | 11/2021 | |
| CN | 214742181 U | 11/2021 | |
| CN | 215566774 U | 1/2022 | |
| CN | 215719690 U | 2/2022 | |
| CN | 215719696 U | 2/2022 | |
| CN | 215860859 U | 2/2022 | |
| CN | 215908080 U | 2/2022 | |
| CN | 215927841 U | 3/2022 | |
| JP | 3220810 U | 4/2019 | |
| JP | 3230942 U | 3/2021 | |
| KR | 20130033865 A | 4/2013 | |
| KR | 20170126376 A | 11/2017 | |
| KR | 20200046236 A | 5/2020 | |
| TW | M537891 U | 3/2017 | |

OTHER PUBLICATIONS

Final Office Action, U.S. Appl. No. 17/585,594, dated Jun. 22, 2022 (26 pages).
International search report and Written Opinion of the International Searching Authority, International Patent Application No. PCT/CN2022/086120, dated Jul. 15, 2022 (16 pages).
Final Office Action, U.S. Appl. No. 17/717,139, dated Aug. 25, 2022 (25 pages).
Non Final Office Action, U.S. Appl. No. 17/717,139, dated Jun 22, 2022 (29 pages).
Non Final Office Action, U.S. Appl. No. 17/717,131, dated Aug. 29, 2022 (25 pages).
Final Office Action, U.S. Appl. No. 17/717,131, dated Aug. 29, 2022 (25 pages).
Non Final Office Action, U.S. Appl. No. 17/739,081, dated Sep. 22, 2022 (126 pages).
Non Final Office Action, U.S. Appl. No. 17/585,594, dated Dec. 22, 2022 (60 pages).
Advisory Office Action, U.S. Appl. No. 17/717,131, dated Dec. 22, 2022 (9 pages).
Advisory Office Action, U.S. Appl. No. 17/717,131, dated Feb. 2, 2023 (7 pages).
Advisory Office Action, U.S. Appl. No. 17/717,139, dated Jan. 11, 2023 (18 pages).
Advisory Office Action, U.S. Appl. No. 17/717,139, dated Mar. 1, 2023 (5 pages).
Japanese Decision of Refusal, Japanese Patent Application No. 2022-514282, dated Feb. 7, 2023 (4 pages).
Final Office Action, U.S. Appl. No. 17/739,081, dated Mar. 7, 2023 (33 pages).

\* cited by examiner
† cited by third party

NECK FAN

CROSS-REFERENCE TO RELATED APPLICATIONS

The application is a continuation of International Application No. PCT/CN2020/128564 filed on Nov. 13, 2020, which claims priority of Chinese patent application 202022210032.8, filed on Sep. 30, 2020, under 35 U.S.C. § 371, both applications are incorporated herein by reference in their entireties.

FIELD

The subject matter herein generally relates to fans, and particularly relates to a fan hanging around a neck.

BACKGROUND

In recent years, people are increasingly pursuing a more convenient life. In order to meet needs of practical fans for outdoor activities or other life scenes, there are a variety of portable fans in the market, such as neck fans. The emergence of neck fans solves limited activity due to handheld fans. The neck fan can free users' hands and realize cooling anytime and anywhere without holding it, whether during sports, outdoor activities or in office.

Existing neck fan generally has a fan assembly with two fan blades exposed at both ends of the neck fan. Such fan assembly not only has low safety that hair is easy to get involved in the fan blades, but also has problems such as outputted air being uncomfortable due to too concentrated air outlets, which needs to be improved.

BRIEF DESCRIPTION OF THE DRAWINGS

Implementations of the present disclosure will now be described, by way of embodiment, with reference to the attached figures. It should be understood, the drawings are shown for illustrative purpose only, for ordinary person skilled in the art, other drawings obtained from these drawings without paying creative labor by an ordinary person skilled in the art should be within scope of the present disclosure.

DETAILED DESCRIPTION

Figure 1:
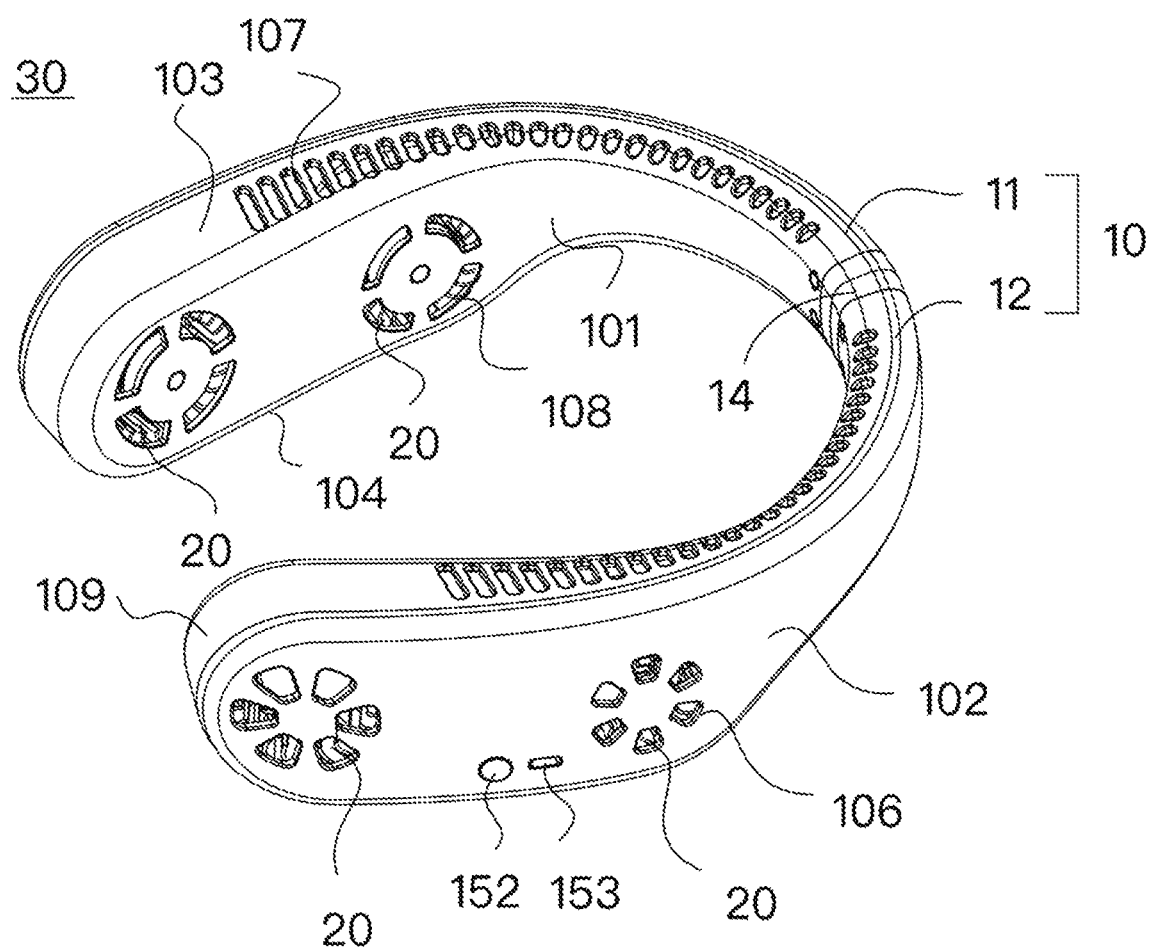
FIG. 1 is a schematic view of a neck fan in according to a first embodiment of the present disclosure.

It will be appreciated that for simplicity and clarity of illustration, where appropriate, reference numerals have been repeated among the different figures to indicate corresponding or analogous elements. In addition, numerous specific details are set forth in order to provide a thorough understanding of the exemplary embodiments described herein. However, it will be understood by those of ordinary skill in the art that the exemplary embodiments described herein may be practiced without these specific details. In other instances, methods, procedures, and components have not been described in detail so as not to obscure the related relevant feature being described. Also, the description is not to be considered as limiting the scope of the exemplary embodiments described herein. The drawings are not necessarily to scale and the proportions of certain parts may be exaggerated to better illustrate details and features of the present disclosure.

The term "comprising" when utilized, means "including, but not necessarily limited to"; it specifically indicates open-ended inclusion or membership in the so-described combination, group, series, and the like. The disclosure is illustrated by way of example and not by way of limitation in the figures of the accompanying drawings in which like references indicate similar elements. It should be noted that references to "an" or "one" embodiment in this disclosure are not necessarily to the same embodiment, and such references can mean "at least one". In addition, the terms "first" and "second" are used for descriptive purposes only and cannot be understood as indicating or implying relative importance or implying the number of indicated technical features. Thus, the features defined as "first" and "second" may explicitly or implicitly include one or more of the said features. In the description of embodiments of the invention, "a plurality of" means two or more, unless otherwise specifically defined.

Embodiment One

Figure 2:
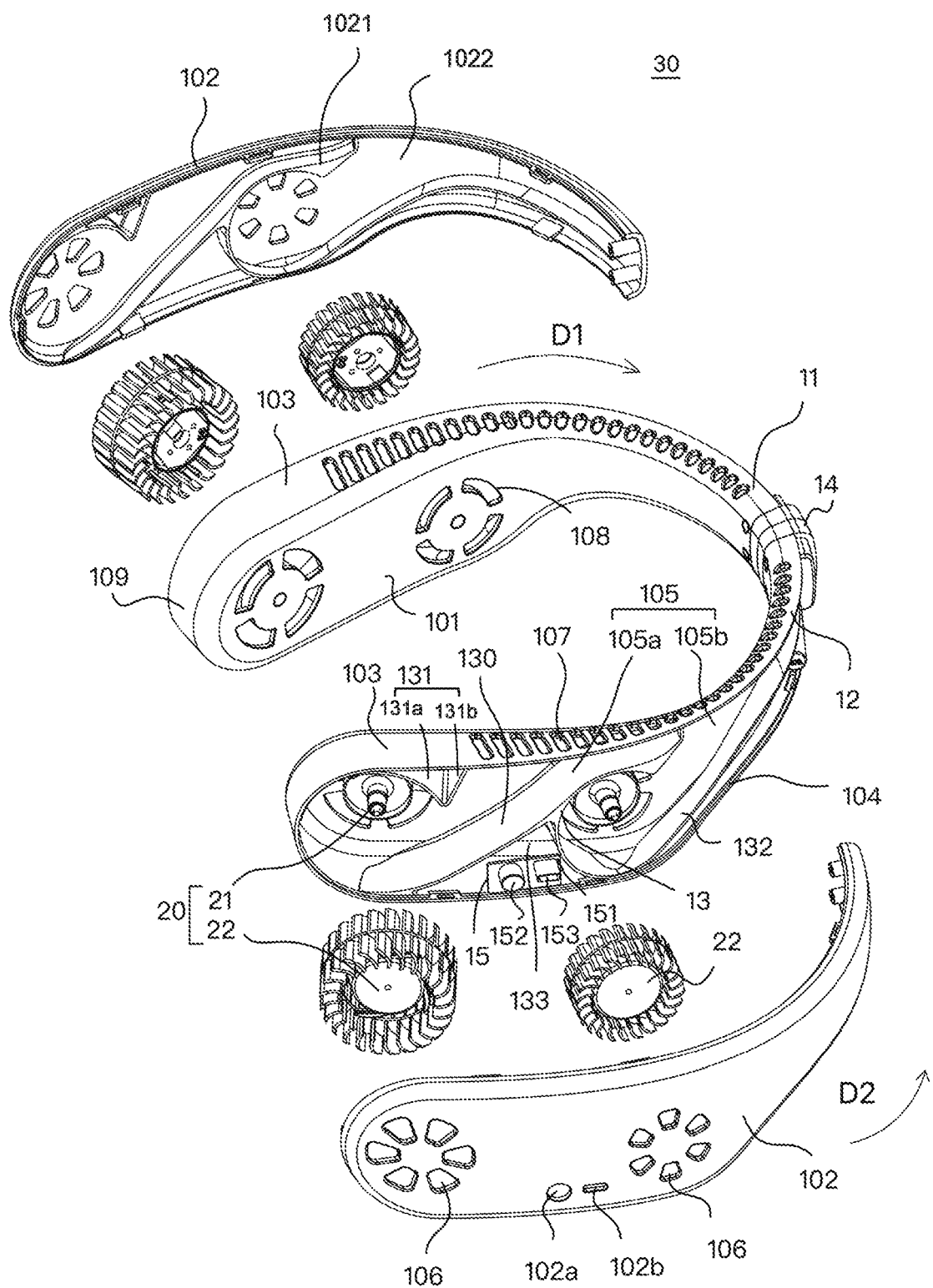
FIG. 2 is an exploded view of the neck fan of FIG. 1.

Referring to FIGS. 1-2, FIG. 1 shows a schematic view of a neck fan provided by a first embodiment of the present disclosure. FIG. 2 show an exploded view of the neck fan of FIG. 1. The neck fan 30 includes an arc-shaped housing 10 and at least four fan assemblies 20. The at least four fan assemblies 20 can be arranged in the arc-shaped housing 10. It should be understood that, for illustration purposes only, in the following embodiment, it is assumed that the number of the at least four fan assemblies is four.

The arc-shaped housing 10 can be hung around user's neck. The arc-shaped housing 10 includes a first part 11 and a second part 12 respectively configured to be hung around two sides of the user's neck. Each of the first part 11 and the second part 12 includes an inner wall 101 configured to be close to the user's neck, an outer wall 102 opposite to the inner wall 101, a top wall 103 interconnecting between the inner wall 101 and the outer wall 102, and a bottom wall 104 interconnecting between the inner wall 101 and the outer wall 102.

The inner wall 101, the outer wall 102 together with the top wall 103 and the bottom wall 104 form an accommodating space 105. Each of the first part 11 and the second part 102 defines air inlets 106 and air outlets 107 communicating with the accommodating space 105. In detail, in the present disclosure, the inner wall 101, the bottom wall 104, and the top wall 103 can be connected into an integrated structure (for example, an integrally formed structure) to form a first side wall. The outer wall 102 can be taken as a second side wall opposite to the first side wall. The first side wall and the second side wall surround the accommodating space 105.

At least one partition 13 is arranged inside the accommodating space 105 to divide the accommodating space 105 into at least two accommodating parts (such as accommodating parts 105a and 105b) which are arranged in turn along an extension direction of the arc-shaped housing 10. Each of the at least two accommodating parts correspond to part of the air inlets 106 and parts of the air outlets 107. Each of the fan assemblies is arranged in a corresponding accommodating part. Each of the fan assemblies is configured to guide air to go in the corresponding accommodating part through corresponding air inlets 106 and guide air to go out of the corresponding accommodating part through corresponding air outlets 107. The number of the air outlets 107 is multiple and multiple air outlets are arranged along the extension direction of the arc-shaped housing 10. Sizes, shapes of the air outlets 107 and/or distances between each two adjacent air outlets 107 varies gradually along the extension direction of the arc-shaped housing 10.

In comparison to existing neck fans, in the neck fan 30 illustrated in the above-mentioned embodiments, the arc-shaped housing 10 includes the first part 11 and the second part 12 are respectively configured to be around two opposite sides of user's neck. Each of the first part 11 and the second part 12 define an accommodating space 105 and air inlets 106, air outlets 107 communicating with the accommodating space 105. Each accommodating space 105 is divided into at least two accommodating parts by the at least one partition 13. Each fan assembly 20 is arranged in a corresponding accommodating part and configured to guide air to go into the corresponding accommodating part through the air inlets 106 and guide air to go out of the corresponding accommodating part through the air outlets 107. Since the fan assemblies 20 are arranged in the accommodating space 105, foreign matters such as hair are not easy to be involved in the fan assemblies, which can improve safety and convenience of use. In at least one embodiment, four fan assemblies 20 are respectively accommodated in four accommodating parts arranged along the extension direction of the arc-shaped housing 10. Since the accommodating space 105 is divided into multiple accommodating parts, an air duct in each accommodating part is relatively short, which not only reduce concentration of outputted air to make outputted air more comfortable but also reduce noise and reduce air volume loss when air is guided into, through and out of each accommodating part. The inventors of the present disclosure find that, the longer the air duct, the longer air flows through the accommodating part, and the greater the noise and air volume loss. By dividing the accommodating space 105 into multiple accommodating parts, voice and air volume loss can be greatly improved. By design of extension directions, sizes, shapes of air outlets 107 and distances between two adjacent air outlets 107, air outputted out from the neck fan 30 is more comfortable and softer, thereby improving user's experiences.

In at least one further embodiment, a size of the air duct decreases gradually along a direction away from corresponding fan assembly. That is, the farther away the air outlet from the fan assembly is, the smaller the size of the air duct is. Such arrangement makes air outputted from the air outlets more uniform.

In at least one further embodiment, each fan assembly 20 includes a driving axis 21 and a fan blade assembly 22 mounted on the driving axis 21. The driving axis extends from the inner wall 101 towards the outer wall 102, which can reduce a thickness of the arc-shaped housing 10 along a direction from the inner wall 101 to the outer wall 102, thereby improving comfort.

In at least one further embodiment, the air inlets 106 are defined at the outer wall 102, and the air outlets 107 are defined at the top wall 103. It should be understood that, the air inlets 106 are defined at the outer wall 102 and the outer wall 102 face outwards, which is benefit for entrance of air and make entrance of air smooth. The air inlets 106 arranged on the outer wall 102, together with the air outlets 107 arranged on the top wall 103 and the drive shaft 21 extending from the inner wall 101 towards the outer wall 102, can make the fan blade assemblies 20 direct the air from the air inlets 106 to the air outlets 107 to achieve a high air guiding efficiency. Moreover, the air outlets 107 is arranged on the top wall 103, which makes outputted air towards user's face and head, thereby achieving rapid cooling effect.

In at least one further embodiment, one end of the driving axis 21 is mounted on the inner wall 101. It should be understood that, such arrangement together with the air inlets 106 arranged at the outer wall 102, make the air inlet 106 not blocked, thereby achieving better air inlet effect.

In at least one further embodiment, each fan assembly 20 corresponds to a plurality of air inlets 106. It should be understood that, air is guided into the fan assembly 20 through the plurality of fan inlets 106, which make the neck fan more beautiful, and is not easy to get foreign matters involved in, thereby increasing safety.

In at least one further embodiment, the number of the air inlets 106 corresponding to each fan assembly 20 is the same. The air inlets 106 corresponding to each fan assembly 20 are arranged in a circular shape. It should be understood that, such arrangement not only makes the appearance of the neck fan beautiful and not easy to have foreign matters involved, but also can cooperate with the shape of the fan assembly 20 to achieve better air inlet effect.

In at least one further embodiment, a plurality of vents 108 are arranged at the inner wall 101 corresponding to each fan assembly 20 and configured to allow air enter therethrough into corresponding accommodating part. Each of the plurality of vents 108 is arc shaped. The plurality of vents 108 corresponding to each fan assembly 20 is arranged in a circular shape. It should be understood that, such arrangement not only makes the appearance of the neck fan beautiful and not easy to have foreign matters involved, but also can cooperate with the shape of the fan assembly 20 to achieve better ventilating effect. The air inlets 106 are arranged at the outer wall 102 and the vents 108 are arranged at the inner wall 101. That is, the air inlets 106 and the vents 108 are arranged at two opposite sides of the arc-shaped housing 10, which greatly improves air inlet efficiency and achieve high air guiding effect.

In at least one further embodiment, the driving axis 21 extends along a direction from the air inlets 106 to the vents 108, which can further improve air inlet efficiency and achieve high air guiding effect.

In at least one further embodiment, the fan blade assembly 22 is a turbine fan blade assembly. It is understandable that the turbine fan blade assembly can achieve lower noise and higher safety.

In at least one further embodiment, the neck fan 30 further includes a connecting part 14 connected between the first part 11 and the second part 12. The connecting part 14 is configured to couple the first part 11 and the second part 12 into an integrated structure. In the present disclosure, the connecting part 14 can be formed individually. However, in other embodiments, the connecting part 14 can be integrally formed with one of the first part 11 and the second part 12, and then assembled with the other of the first part 11 and the second part 12. Since the structure of the connecting part 14 can be diverse, it is not limited in the present disclosure.

Each of the first part 11 and the second part 12 further includes an end plate 109 at an end thereof away from the connecting part 14. Sizes of the air inlets 106 corresponding to the fan assembly 20 arranged near the connecting part 14 are less than those of the air inlets 106 corresponding to the fan assembly 20 arranged near the end plate 19. An outer diameter of the fan assembly 20 arranged near the connecting part 14 is less that that of the fan assembly 20 arranged near the end plate 19. In other words, an end of each of the first part 11 and the second part 12 connected with the connecting part 14 can be considered as a connecting end, and an end of each of the first part 11 and the second part 12 connected with the end plate 109 can be considered as a free end. Sizes of the air inlets 106 near the connecting end is less than those of the air inlets 106 near the free end. An outer diameter of the fan assembly 20 near the connecting end is less that of the fan assembly 20 near the free end. It should be understood that, through the design of air inlets 106 of different sizes and the outer diameters of the fan assemblies 20 of different sizes, the size of the arc-shaped housing 10 can be gradually reduced along a direction from the end plate 109 to the connecting part 14, which is more suitable for the curve of human neck and increases comfort of wearing. In this embodiment, the end plate 109 is arc shaped, which not only has good aesthetics and comfort, but also can match shapes of the accommodating parts and shapes of the fan assemblies 20 to achieve better air inlet and outlet effect.

It should be understood that, for each of the first part 11 or the second part 12, the inner wall 101, the top wall 103, the bottom wall 104, the end plate 109, and the at least one partition 13 can be integrally formed. The outer wall 102 can be assembled with the top wall 103, the bottom wall 104, the end plate 109 with fasteners. Structures of the fasteners can be diverse, it is not limited in the present disclosure.

In at least one further embodiment, the number of the air outlets 107 is multiple and multiple air outlets 107 are arranged along the extension direction of the arc-shaped housing 10 and extends to near the connecting part 14. Sizes of the air outlets 107 gradually decrease along a direction from the end plate 109 to the connecting part 14. It should be understood, multiple air outlets 107 can improve safety. Sizes of the air outlets 107 gradually decrease along a direction from the end plate 109 to the connecting part 14, which is beneficial for concentration of air, improve the air outlet intensity. The air outlets 107 further cooperate with the accommodating parts (for example, 105a and 105b) inside which air volume along an extension direction of the air duct is gradually reduced to make the overall air outlet more uniform and comfortable. In detail, a direction from the first part 11 to the second part 12 is defined as a first extension direction D1, sizes of the multiple air outlets 107 defined at the first part 11 are gradually reduced along the first extension direction D1. A direction from the second part 12 to the first part 11 is defined as a second extension direction D2. Sizes of the multiple air outlets 107 defined at the second part 12 are gradually reduced along the second extension direction D2. Furthermore, each of the air outlets 107 is a strip air outlet, an extension direction of the strip air inlet together with the extension direction of the arc-shaped housing 10 define a preset angle. The preset angle can be 90 degree. It can be understood that through the design of the air outlets 107 in the above extension direction, the air outlet of the neck fan 30 can be more comfortable and softer, thereby improving user's use experience. In particular, the preset angle is 90 degrees, which can improve the air outlet efficiency of the air outlets 107.

In at least one further embodiment, each of the at least one partition 13 is connected to a surface of the inner wall 101 towards the outer wall 102 and extends towards the outer wall 102, each of the at least one partition 13 includes a main body 130, a first guiding part 131, and a second guiding part 132. One end of the main body 130 is connected to the bottom wall 104 adjacent to the end plate 109, and the other end of the main body 130 extends towards a middle of the top wall 103 to be close to the middle of the top wall 103. The first guiding part 131 includes a first portion 131a around the fan assembly 20 adjacent to the end plate 109 and a second portion 131b connected between the first portion 131a and the top wall 103. The second guiding part 132 is connected to the main body 130 and around the fan assembly 20 adjacent to the connecting part 14. It should be understood that, the main body 130 is configured to divide the accommodating space 105 to accommodating parts (for example, 105a, 105b), the first guiding part 131 and the second guiding part 132 are configured to match shapes of the fan blade assemblies 22 so as to guide air and achieve a better air outlet effect.

In at least one further embodiment, an end of the second guiding part 132 away from the main body 130 extends to the connecting part 14. Along a direction from the end plate 109 to the connecting part 14, a distance between the second guiding part 132 and the bottom wall 103 are gradually reduced until the second guiding part 132 is tangent to the bottom wall 103, and then the distance between the second guiding part 132 and the bottom wall 103 are gradually increased to a predetermined value and remained at the predetermined value. The predetermined value can be determined according to actual requirements. In at least one embodiment, the predetermined value can be an half of a distance between the top wall 103 and the bottom wall 104. Such arrangement of the second guiding part 132 can make the air duct extend to the connecting part 14. Such arrangement cooperates with the air outlets 107 adjacent to the connecting part 14 to make air outlet range of the neck fan 30 larger and improve cooling effect.

In at least one further embodiment, the neck fan 30 further includes electronic components 15. The electronic components 15 include battery (not shown) and printed circuit board 151. The second guiding part 132 cooperates with the main body 130 to define a receiving space 133 configured to receive at least part of the electronic components 15. It should be understood, the electronic components 15 are received in the receiving space 133, which can avoid heat generated by the electronic components 15 to go into the accommodating parts, thereby avoiding negative effects on cooling. In addition, such arrangement allows individually design of heat dissipation and wiring of the electronic components 15, thereby improving safety.

In at least one further embodiment, the electronic components 15 further includes a switch button 152 and a data port 153. The outer wall 102 of the second part 12 defines a first opening 102a corresponding to the switch button 152 and a second opening 102b corresponding to the data port 153. The switch button 152 is mounted on the outer wall 102 corresponding to the first opening 102a and connected to the printed circuit board 151, and the data port 153 is mounted on the outer wall 102 corresponding to the second opening 102b and connected to the printed circuit board 151. Such arrangement is convenient for users to operate, thereby improving user's experience. Furthermore, it should be understood, apart from the electronic components 15, the structures and elements of the first part 11 and the second part 12 are symmetrically arranged to increase wearing comfort.

In at least one further embodiment, the outer wall 102 includes a main plate 1021 and an auxiliary plate 1022. The shape and position of the auxiliary plate 1021 correspond to those of the partition 13, and the auxiliary plate 1021 is connected between the main plate 1021 and the partition 13. It can be understood that the auxiliary plate 1022 can further cooperate with the partition 13 to define the air duct of the fan assembly 20, so as to achieve a better air guiding effect.

Embodiment Two

Figure 3:
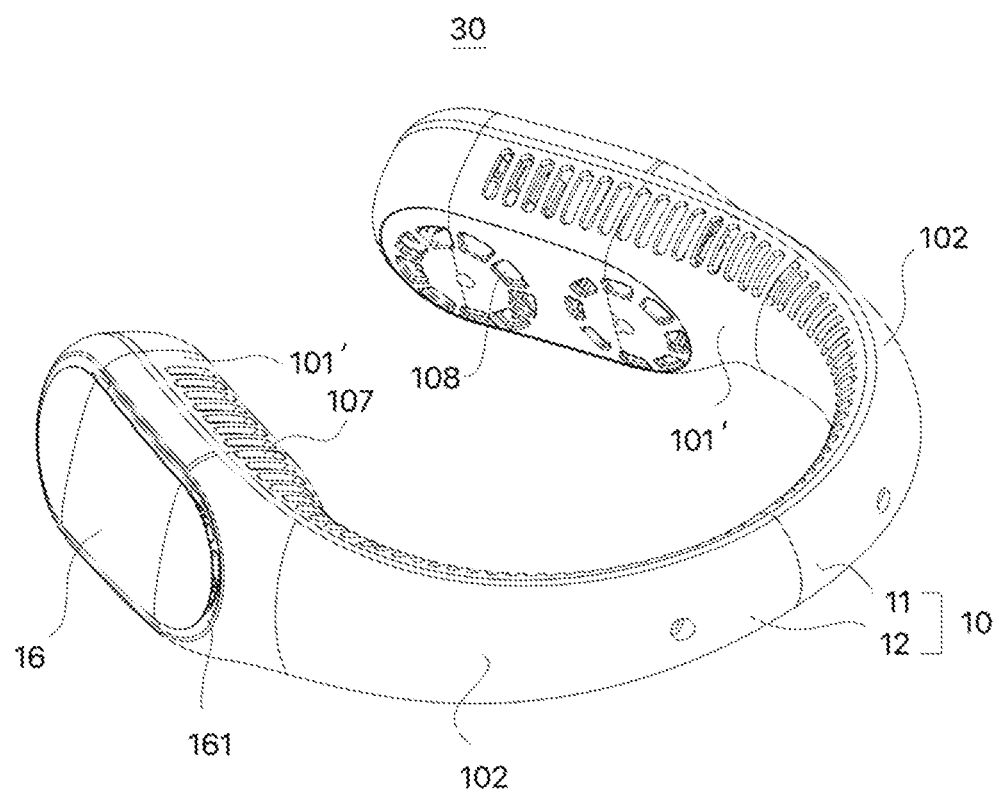
FIG. 3 is a schematic view of a neck fan in according to a second embodiment of the present disclosure.
Figure 4:
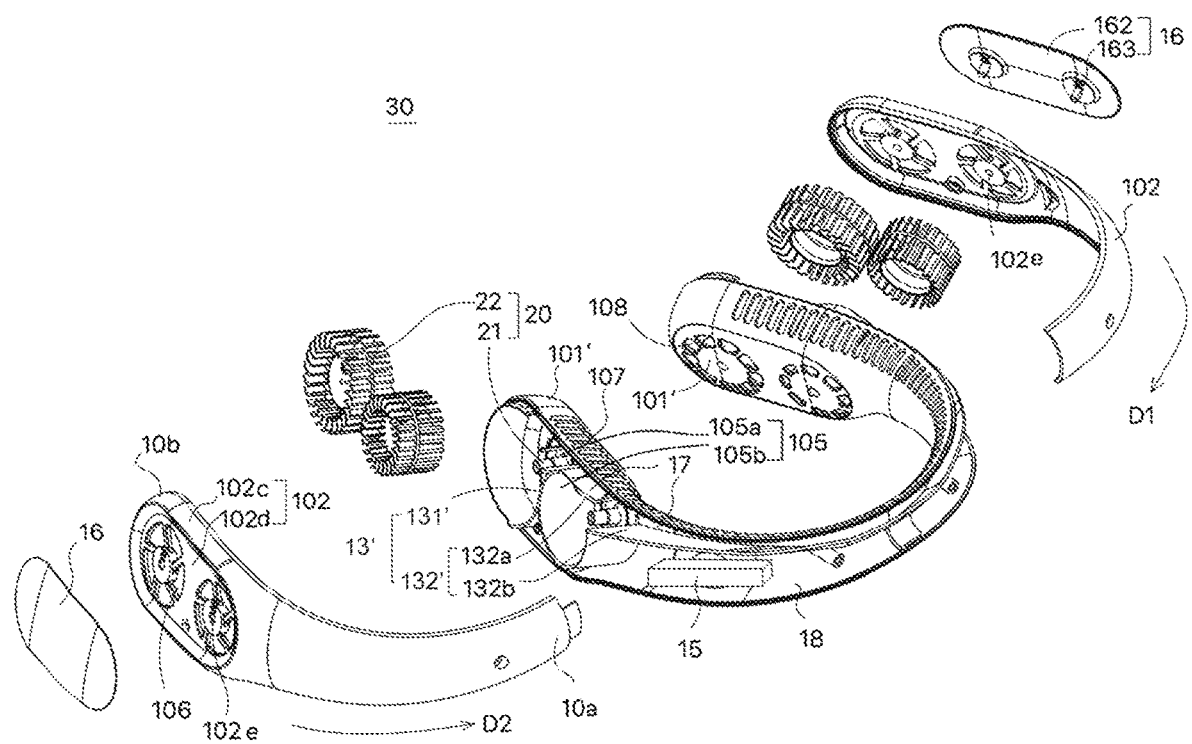
FIG. 4 is an exploded view of the neck fan of FIG. 3.
Figure 5:
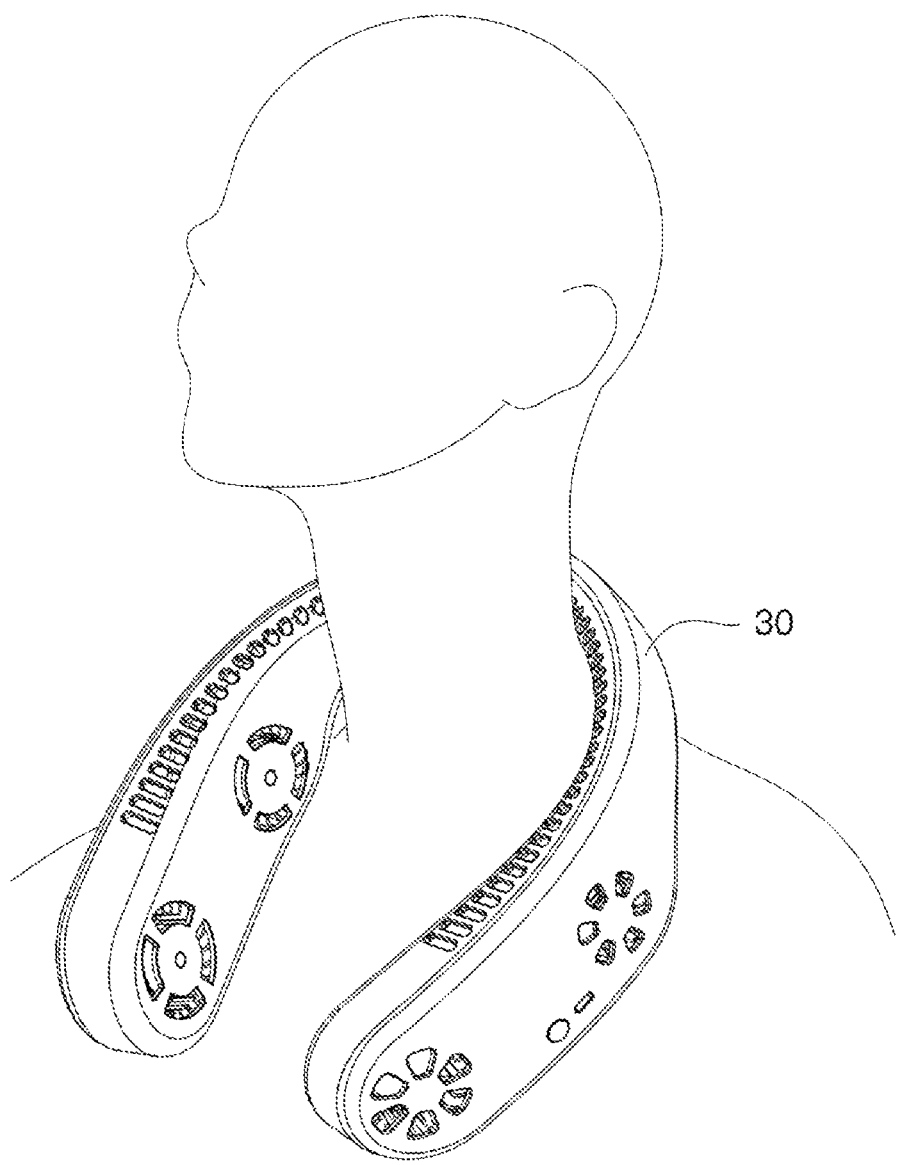

Referring to FIGS. 3 and 4, FIG. 3 is a schematic view of a neck fan 30 according to a second embodiment of the present disclosure. FIG. 4 is an exploded view of the neck fan 30 of FIG. 3. The neck fan 30 includes an arc-shaped housing 10 and at least four fan assemblies 20. The at least four fan assemblies 20 are arranged inside the arc-shaped housing 10. It should be understood that in the present embodiment, it is assumed that the number of the at least four fan assemblies 20 is four.

The arc-shaped housing 10 can be hung around user's neck. The arc-shaped housing 10 includes a first part 11 and a second part 12. The first part 11 and the second part 12 are respectively configured to surround two opposite sides of user's neck. Both the first part 11 and the second part 12 include sidewalls surrounding an accommodating space 105. Each of the first part 11 and the second part 12 defines air inlets 106 and air outlets 107 communicating with the accommodating space 105.

At least one partition 13 is arranged in the accommodating space 105 and configured to divide the accommodating space 105 to at least two accommodating parts (such as 105a, 105b) arranged along an extension direction of the arc-shaped housing 10. Each of the at least two accommodating parts corresponds a part of the air inlets 106 and a part of the air outlets 107. Each fan assembly 20 is located in corresponding one of the at least two accommodating parts. Each fan assembly 20 is configured to direct air into corresponding accommodating part through the air inlets 106 and direct air out of the corresponding accommodating part through the air outlets 107. The number of the air outlets 107 is multiple and multiple air outlets 107 are arranged along the extension direction of the arc-shaped housing 10. Sizes, shapes of the air outlets 107 and/or distances between each two adjacent air outlets 107 varies gradually along the extension direction of the arc-shaped housing 10.

In comparison to existing neck fans, in the neck fan 30 illustrated in the above-mentioned embodiments, the arc-shaped housing 10 includes the first part 11 and the second part 12 are respectively configured to be around two opposite sides of user's neck. Each of the first part 11 and the second part 12 define an accommodating space 105 and air inlets 106, air outlets 107 communicating with the accommodating space 105. Each accommodating space 105 is divided into at least two accommodating parts by the at least one partition 13. The at least one partition 13 together with the sidewalls defines at least two air ducts located in the at least two accommodating parts respectively. Each fan assembly 20 is arranged in a corresponding accommodating part and configured to guide air to go into the corresponding accommodating part through the air inlets 106 and guide air to go out of the corresponding accommodating part through the air outlets 107. Since the fan assemblies 20 are arranged in the accommodating space 105, foreign matters such as hair are not easy to be involved in the fan assemblies, which can improve safety and convenience of use. In at least one embodiment, four fan assemblies 20 are respectively accommodated in four accommodating parts arranged along the extension direction of the arc-shaped housing 10. Since the accommodating space 105 is divided into multiple accommodating parts, the air duct in each accommodating part is relatively short, which not only reduce concentration of outputted air to make outputted air more comfortable but also reduce noise and reduce air volume loss when air is guided into, through and out of each accommodating part. The inventors of the present disclosure find that, the longer the air duct, the longer air flows through the accommodating part, and the greater the noise and air volume loss. By dividing the accommodating space 105 into multiple accommodating parts, voice and air volume loss can be greatly improved. By design of extension directions, sizes, shapes of air outlets 107 and distances between two adjacent air outlets 107, air outputted out from the neck fan 30 is more comfortable and softer, thereby improving user's experiences.

In detail, the sidewalls include a first sidewall 101' configured to be close to the user's neck, a second sidewall 102 opposite to the first sidewall 101. The air inlets 106 are arranged at the second sidewall 102, and the air outlets 107 are arranged at the first sidewall 101' adjacent to the second sidewall 102 or arranged at the second sidewall 102 adjacent to the first sidewall 101'. In the present embodiment, the air outlets 107 are arranged at the first sidewall 101' adjacent to the second sidewall 102 and configured to be close to user's head and face.

In at least one further embodiment, a direction from the first part 11 to the second part 12 is defined as a first extension direction D1, sizes of the air outlets 107 on the first part 11 reduce gradually along the first extension direction D1. A direction from the second part 12 to the first part 11 is defined as a second extension direction D2, sizes of the air outlets 107 on the second part 12 reduce gradually along the second extension direction D2. Furthermore, each of the air outlets 107 is a strip air outlet, an extension direction of the strip air inlet together with the extension direction of the arc-shaped housing 10 define a preset angle. The preset angle can be 90 degrees. It can be understood that through the design of the air outlets 107 in the above extension direction, the air outlet of the neck fan 30 can be more comfortable and softer, thereby improving user's use experience. In particular, the preset angle is 90 degrees, which can improve air outlet efficiency of the air outlets 107. In other embodiments, shapes of the air outlets 107 can be at least one of petal shape and heart shape. It should be understood that, air outlets 107 in petal shape or heart shape not only have advantages of air outlet uniformity but also is more beautiful.

In at least one further embodiment, a size of the air duct decreases gradually along a direction away from corresponding fan assembly. That is, the farther away the air outlet from the fan assembly is, the smaller the size of the air duct is. Such arrangement makes air outputted from the air outlets more uniform.

In at least one further embodiment, each fan assembly 20 includes a driving axis 21 and a fan blade assembly 22 mounted on the driving axis 21. The driving axis 21 extends along a direction from the first sidewall 101' to the second sidewall 102, which can reduce a thickness of the arc-shaped housing 10 along a direction from the inner wall 101 to the outer wall 102, thereby improving comfort.

It should be understood, the air inlets 106 are arranged at the second sidewall 102 and the second sidewall 102 faces outwards, which is beneficial for air inlet, thereby making air inlet smoothly. Such arrangement cooperates with the air outlets 107 close to user's head and face and the driving axis 21 extending along the direction from the first sidewall 101' to the second sidewall 102, which is beneficial for the fan blade assembly 22 to direct air from the air inlets 106 to the air outlets 107, thereby achieving a relatively high air guiding efficiency. Moreover, the air outlets 107 are arranged at the first sidewall 101' close to user's head and face, which is beneficial for directing air out towards user's head and face, thereby achieving better cooling effect.

The first sidewall 101' defines a plurality of vents 108 corresponding to each fan assembly 20 and configured to allow air enter therethrough into corresponding accommodating part. Each of the plurality of vents 108 is arc shaped.

The plurality of vents 108 corresponding to each fan assembly are arranged in a circular shape. It should be understood, such arrangement not only makes appearance of the neck fan 30 beautiful, but also is not easy to get foreign matters involved in the fan assembly 20. Such arrangement cooperates with shapes of the fan assemblies 20 can achieve better ventilation effect. The air inlets 106 are arranged at the second sidewall 102 and the vents 108 are arranged at the first sidewall 101'. That is, the air inlets 106 and the vents 108 are arranged at two opposite sides of the arc-shaped housing 10, which greatly improves air inlet efficiency and achieve high air guiding effect.

In at least one further embodiment, the driving axis 21 extends along a direction from the air inlets 106 to the vents 108, which can further improve air inlet efficiency and achieve high air guiding effect.

In at least one further embodiment, each one of the first part 11 and the second part 12 has a connecting end 10a connected with the other of the first part 11 and the second part 12, and a free end 10b away from the connecting end 10a. Sizes of the air outlets 107 corresponding to the fan assembly 20 adjacent to the connecting end 10a are less than those of the air outlets 107 corresponding to the fan assembly 20 adjacent to the free end 10b. An outer diameter of the fan blade assembly 22 adjacent to the connecting end 10a is less than that of the fan blade assembly 22 adjacent to the free end 10b. It should be understood, through designs of sizes of the air inlets 106 and design of sizes of the fan blade assembly 22, a size of the arc-shaped housing 10 can reduce gradually along a direction from the free end 10b to the connecting end 10a, which is better to fit curve of user's neck, thereby increasing wearing comfort.

Each of the first part 11 and the second part 12 includes a cover 16. The cover 16 is connected to the second sidewall 102 away from the first sidewall 101' and configured to correspond to the air inlets 106. A gap 161 communicated with the air inlets 106 is defined between edges of the cover 16 and the second sidewall 102 to allow air to go therethrough into the air inlets 106. In addition, the second sidewall 102 includes a main part 102c, and a recessed par 102d connected to the main part 102c and recessed towards the first sidewall 101'. The air inlets 106 are arranged at the recessed part 102d. The cover 16 covers the recessed part 102d. The cover 16 is partially connected to edges of the main part 102c connected to the recessed part 102d so as to form the gap 161. It should be understood, the cover 16 covers the air inlets 106, and air enters through the gap 161 and the air inlets 106, which not only has a beautiful appearance, but also is not easy to get foreign matters involved in and increases safety. The design of the recessed part 102d is also conducive to reduce the overall size of the neck fan 30 and to increase the appearance aesthetics.

In at least one further embodiment, the cover 16 can include a cover body 162, and a first mounting part 163 arranged at the cover body 162 adjacent to the second sidewall 102. The second sidewall 102 is provided with a second mounting part 102e. In detail, the second mounting part 102e can be arranged at the recessed part 102d and is located among a plurality of air inlets 106.

In at least one further embodiment, the first mounting part 163 cooperates with the second mounting part 102e to mount the cover 16 (for example, detachably or movable mount) on the second sidewall 102 away from the first sidewall 101'. It should be understood, through the first mounting part 163 cooperating with the second mounting part 102e, the cover 16 can be detachably or movably mounted onto the second sidewall 102, which is easy to mount/dismount and use.

In at least one further embodiment, the first mounting part 163 and the second mounting part 102e can be switched between a first mounting state and a second mounting state. In the first mounting state, the gap 161 is formed between edges of the cover 16 and the second sidewall 102. In the second mounting state, the edges of the cover 16 resists against the second sidewall 102 so as to seal the air inlets 106. It should be understood, by design of the first mounting state where air can enter the accommodating part through the gap 161 and the air inlets 106 and the second mounting state where the gap 161 is closed and the air inlets 106 are sealed, therefore, dust can be prevented from entering the arc-shaped housing through the air inlets 106 when the neck fan 30 is not in use to achieve the effect of dust prevention.

It should be understood, the first mounting state and the second mounting state can be switched from one to the other. In at least one embodiment, the first mounting part and the second mounting part can employ fasteners such as elastic buckles to switch the first mounting state and the second mounting state. For example, when the cover 16 is applied a force towards the second sidewall 102, it is switched from the first mounting state to the second mounting state, and when the force towards the second sidewall 102 is again applied on the cover 16, it is switched from the second mounting state to the first mounting state. Structures configured to switch the first mounting state and the second mounting state can be diverse, and it is not limited in the present disclosure.

In the present embodiment, the first mounting part 163 can be a mounting shaft connected to the cover body 162, and the second mounting part 102e can be a mounting hole corresponding to the mounting shaft. In other embodiments, the first mounting part 163 can be a mounting hole defined at the cover body 162, and the second mounting part 102e can be a mounting shaft corresponding to the mounting hole. It should be understood, through the mounting hole cooperating with the mounting shaft, the cover 16 is mounted onto the second sidewall 102, which is easy to mount.

In the present embodiment, each of the at least one partition 13' includes a main body 131' and a guiding part 132'. A shape of the main body 131' at least partially matches to the fan assembly 20 and surrounds the fan assembly 20. The guiding part 132' is connected to the main body 131' and configured to cooperate with the sidewalls to define air ducts 17 communicated with the air outlets 107. It should be understood, the main body 131' matches to the fan assembly 20, and the guiding part 132' cooperates with the sidewalls to define the air ducts 17 communicated with the air outlets 107, which can achieve a better guiding effect and improve air inlet efficiency.

In at least one further embodiment, in each of the first part 11 and the second part 12, the guiding part 132' includes a first guiding portion 132a located between two fan assemblies 20 and a second guiding portion 132b arranged at a side of one of the two fan assemblies 20 away from the other of the two fan assemblies. The second guiding part 132b extends from one of the first part 11 and the second part 12 to the other of the first part 11 and the second part 12. A side of the second guiding portion 132b cooperates with the sidewalls to form a receiving space 18. The neck fan 30 further includes electronic components 15. The electronic components 15 can include a battery and a printed circuit board. The receiving space 18 is configured to receive at least one of the battery and the printed circuit board. It should be understood, by arranging the electronic components 15 in the receiving space 18, configuration of the neck fan 30 can be effectively balanced and wearing comfort can be improved.

In at least one embodiment, the fan blade assembly 20 can be a turbine fan blade assembly. It is understandable that the turbine fan blade assembly can achieve lower noise and higher safety.

The above description only describes embodiments of the present disclosure, and is not intended to limit the present disclosure, various modifications and changes can be made to the present disclosure. Any modifications, equivalent substitutions, improvements, etc. made within the spirit and scope of the present disclosure are intended to be included within the scope of the present disclosure.

What is claimed is:

1. A neck fan, comprising:
   an arc-shaped housing, configured to hang around a user's neck, wherein the arc-shaped housing comprises a first part and a second part respectively configured to be around two opposite sides of the user's neck, each of the first part and the second part comprises sidewalls surrounding an accommodating space, each of the first part and the second part further defines air inlets and air outlets communicated with the accommodating space, a partition is arranged in the accommodating space and configured to divide the accommodating space into two accommodating parts arranged along an extension direction of the arc-shaped housing, one of the two accommodating parts corresponds to the air inlets and the air outlets; and
   a plurality of fan assemblies, wherein each of the plurality of fan assemblies is received in the accommodating space, and each of the plurality of fan assemblies is configured to direct air into one of the two accommodating parts corresponding to the air inlets and to direct air out of the one of the two accommodating parts through corresponding air outlets, the number of the air outlets is multiple, and multiple air outlets are arranged along the extension direction of the arc-shaped housing;
   wherein the plurality of fan assemblies comprise a first fan assembly and a second fan assembly;
   each of the sidewalls comprises an inner wall disposed near the user's neck and an outer wall opposite to the inner wall and disposed away from the user's neck; and
   the air inlets are defined in each of the inner wall and the outer wall.

2. The neck fan according to claim 1, wherein a direction from the first part to the second part is a first extension direction, multiple air outlets on the first part reduce along the first extension direction; a direction from the second part to the first part is a second extension direction, and multiple air outlets on the second part reduce along the second direction; or
   each of the air outlets is a strip air outlet, an extension direction of the strip air outlet and the extension direction of the arc-shaped housing defines an angle which is 90 degrees; or
   the air outlets are in shapes selected from at least one of a petal shape or a heart shape.

3. The neck fan according to claim 1, wherein the air outlets are arranged at the position of the inner wall adjacent to the second sidewall or arranged at a position of the outer wall adjacent to the inner wall.

4. The neck fan according to claim 3, wherein each fan assembly corresponds to multiple air inlets, each fan assembly corresponds to the same number of air inlets, the multiple air inlets corresponding to each fan assembly are arranged in a circular shape, the first sidewall defines a plurality of vents corresponding to each fan assembly, each of the plurality of vents is arc shaped, the plurality of vents corresponding to each fan assembly are arranged in a circular shape.

5. The neck fan according to claim 3, wherein each one of the first part and the second part comprises a connecting end connected to the other of the first part and the second part and a free end away from the connecting end, sizes of the air inlets corresponding to the fan assembly adjacent to the connecting end are less than those of the air inlets corresponding to the fan assembly adjacent to the free end, an outer diameter of the fan assembly adjacent to the connecting end is less than that of the fan assembly adjacent to the free end.

6. The neck fan according to claim 3, wherein each of the first part and the second part comprises a cover corresponding to the air inlets and the cover is connected to the second sidewall away from the first sidewall, a gap is defined between edges of the cover and the second sidewall.

7. The neck fan according to claim 6, wherein the second sidewall comprises a main part and a recessed part connected to the main part and recessed towards the first sidewall, the air inlets are arranged at the recessed part, the cover covers the recessed part, the cover is at least partially connected to the main part adjacent to the recessed part to define the gap.

8. The neck fan according to claim 6, wherein the cover comprises a cover body and a first mounting part arranged at the cover body, the second sidewall is provided with a second mounting part corresponding to the first mounting part, the first mounting part cooperates with the second mounting part to detachably or movably mount the cover onto the second sidewall away from the first sidewall.

9. The neck fan according to claim 8, wherein the first mounting part and the second mounting part are switched between a first mounting state where the edges of the cover and the second sidewall defines the gap communicating with the air inlets and a second mounting state where the edges of the cover are attached to the second sidewall to seal the air inlets.

10. The neck fan according to claim 8, wherein one of the first mounting part and the second mounting part is a mounting shaft, and the other of the first mounting part and the second mounting part is a mounting hole configured to receive the mounting shaft.

11. The neck fan according to claim 5, wherein each fan assembly comprises a driving axis and a fan blade assembly mounted on the driving axis, the driving axis extends along a direction from the first sidewall to the second sidewall, and the partition is connected to a side of the first sidewall facing the second sidewall and extends towards the second sidewall.

12. The neck fan according to claim 11, wherein the air outlets are arranged at the top wall, one end of the main body is connected to the bottom wall adjacent to the free end, and the other end of the main body extends to a middle of the top wall, in each of the first part and the second part, the first fan assembly is adjacent to the free end, and the second fan assembly is located on a side of the first fan assembly away from the free end.

13. The neck fan according to claim 12, wherein the neck fan further comprises electronic components, the electronic components comprise a battery and a printed circuit board, the second guiding part cooperates with the main body to define a receiving space configured to receive at least part of the electronic components, the electronic components further comprise a switch button and a data port, the second side wall on the second part defines a first opening corresponding to the switch button and a second opening corresponding to the printed circuit board, the switch button is mounted on the second sidewall corresponding to the first opening and connected to the printed circuit board, and the data port is mounted on the second sidewall corresponding to the second opening and connected to the printed circuit board.

14. The neck fan according to claim 12, wherein the second sidewall comprises a main plate and an auxiliary plate, a shape and a position of the auxiliary plate corresponds to those of the partition, and the auxiliary plate is connected between the main plate and the partition.

15. The neck fan according to claim 11, wherein the partition comprises a main body and a guiding part, a shape of the main body at least partially matches to that of the fan assembly and the main body surrounds the fan assembly, the guiding part is configured to cooperate with the sidewalls to surround an air duct communicated with the air outlets.

16. The neck fan according to claim 1, wherein in each of the first part and the second part, the fan assemblies comprises a first fan assembly and a second fan assembly adjacent to the first fan assembly, the guiding part comprises a first guiding portion located between the first fan assembly and the second fan assembly and a second guiding portion located at one side of the second fan assembly away from the first fan assembly, the second guiding portion extends from one of the first part and the second part towards the other of the first part and the second part, a side of the second guiding portion away from the air duct cooperates with the sidewalls to surround a receiving space, the neck fan further comprises electronic components, the electronic components comprises a battery and a printed circuit board, the receiving space is configured to receive at least one of the battery and the printed circuit board.

17. A neck fan, comprising:
a housing, configured to hang around a user's neck; wherein the housing comprises a first part and a second part respectively configured to be around two opposite sides of the user's neck, each of the first part and the second part comprises sidewalls surrounding an accommodating space, each of the first part and the second part further defines air inlets and air outlets communicated with the accommodating space;
a partition, arranged in the accommodating space of each of the first part and the second part and configured to divide the accommodating space into two accommodating parts arranged along an extension direction of the housing;
a plurality of fan assemblies, wherein each of the plurality of fan assemblies is received in one of the two accommodating parts, wherein each of the at least two fan assemblies corresponds to part of the air inlets and part of the air outlets, and is configured to direct air into the corresponding one of the two accommodating parts from the part of the air inlets and then through the corresponding one of the two accommodating parts and direct air out of the corresponding one of the two accommodating parts through the part of the air outlets, wherein the sidewalls of each of the first part and the second part further defines vents corresponding to the air inlets; wherein the air inlets and the vents are arranged at each of a side of housing disposed near the user's neck and a side of the housing disposed away from the user's neck.

18. The neck fan according to claim 17, each of the at least two fan assemblies is a turbine fan assembly and comprises a driving axis and a fan blade assembly mounted on the driving axis, the driving axis extends along a direction from the air inlets to corresponding vents; a size of each of the at least two air ducts decreases along a direction away from a corresponding one of the at least two fan assemblies; the at least two fan assemblies comprises four fan assemblies, two fan assemblies of the four fan assemblies are arranged in the at least two accommodating parts of the first part respectively, the other two fan assemblies of the four fan assemblies are arranged in the at least two accommodating parts of the second part respectively a first cover is connected to the sidewalls of the first part to cover the air inlets corresponding to the two fan assemblies and a first gap is defined between edges of the first cover and the sidewalls of the first part to allow air to go into the air inlets, and a second cover is connected to the sidewalls of the second part to cover the air inlets corresponding to the other two fan assemblies and a second gap is defined between edges of the second cover and the sidewalls of the second part to allow air to go into the air inlets.

* * * * *